United States Statutory Invention Registration [19]

[11] Reg. Number: H255

Genovese et al. [43] Published: Apr. 7, 1987

[54] CHARCOAL ADSORBENT TEST APPARATUS AND METHOD USING FILTER TUBES

[75] Inventors: James A. Genovese, Forest Hill; John T. James, Severn; Leonard C. Buettner, Baltimore, all of Md.

[73] Assignee: The United States of America as represented by the Secretary of the Army, Washington, D.C.

[21] Appl. No.: 900,880

[22] Filed: Aug. 26, 1986

[51] Int. Cl.[4] ..... A61K 49/00; G01N 31/00; G01N 33/48; G01N 30/96

[52] U.S. Cl. ..... 424/9; 436/37; 422/88

*Primary Examiner*—John F. Terapane
*Assistant Examiner*—Susan Wolffe
*Attorney, Agent, or Firm*—Anthony T. Lane; Harold H. Card, Jr.; Edward F. Costigan

[57] ABSTRACT

An apparatus and method for testing the performance of a sample charcoal adsorbent material. The apparatus comprises means for supplying a gaseous sample containing toxic contaminants to a filtering means. The filtering means includes a filter tube containing a sample charcoal adsorbent material for adsorbing the toxic contaminants. Chemical analysis means are included for detecting toxic contaminants remaining in the gaseous effluent from the filtering means. Test animal chambers are also provided for exposing test animals contained therein to the gaseous effluent to determine the toxic effects and breathing rate changes on the test animals caused by toxic or irritating contaminants remaining in the gaseous effluent.

14 Claims, 6 Drawing Figures

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

CHARCOAL ADSORBENT TEST APPARATUS AND METHOD USING FILTER TUBES

The invention described herein may be manufactured, used and licensed by or for the Government for Governmental purposes without the payment to us of any royalties thereon.

FIELD OF THE INVENTION

The present invention relates to an apparatus and a method for evaluating the performance of a sample charcoal adsorbent material. More particularly, the present invention relates to an apparatus and method for testing the ability of a sample charcoal adsorbent material to remove toxic contaminants from a gaseous sample.

BACKGROUND OF THE INVENTION

Charcoal adsorbent materials are well known in the art for removing individual components from gaseous or liquid mixtures. Charcoal adsorbent materials are used in many industrial applications for such separation purposes. Charcoal adsorbent materials are also used in protective gas mask devices in order to provide a safe source of uncontaminated air for breathing in a contaminated environment. In the field of protective gas masks, however, it has been difficult to determine under realistic test conditions how well various types of charcoal adsorbent materials protect against different types of contaminated or toxic gases.

More particularly, the testing of charcoal filter cartridges or canisters included in protective gas masks requires large quantities of test gases and extended analysis time in order to determine the performance of a particular sample charcoal adsorbent material. Additionally, chemical analysis performed on the effluent from the filter cartridges or canisters does not always detect the presence of toxic materials. Similarly, such chemical analysis may indicate the presence of a compound of unknown toxicity. Moreover, to be used effectively as a filter material in a protective gas mask, charcoal adsorbent materials must protect against highly irritating vapors, for example, vapors which irritate eyes, skin and respiratory systems. Chemical analysis of filter effluents may not detect the presence of such irritating materials or may indicate the presence of compounds whose highly irritating properties are not known. Thus, chemical analysis alone often provides an incorrect estimate of the performance and effectiveness of a charcoal adsorbent material for use in a protective gas mask. Accordingly, there is a need for an apparatus and method for quickly and effectively evaluating the performance of various charcoal adsorbent materials.

SUMMARY OF THE INVENTION

It is therefore an object of the present invention to provide a method and apparatus for quickly and effectively evaluating the performance of a sample charcoal adsorbent material.

It is a further object of the invention to provide an apparatus and method for quickly and effectively testing the performance of a sample charcoal material particularly adapted for use in a protective gas mask.

It is a related object to provide an apparatus and method for testing the performance of a sample charcoal adsorbent material by detecting the presence of toxic contaminants remaining in the gaseous effluent from a filter containing the charcoal adsorbent material and by determining the toxicity and irritating properties of the gaseous effluent from the filter containing the charcoal adsorbent material.

It is also an object of the invention to provide a method for testing the performance of a sample charcoal adsorbent material which employs smaller quantities of sample gases than known methods and which requires reduced analysis time as compared with known methods.

These and other objects and advantages are provided by the apparatus and method of the present invention. The apparatus comprises means for supplying a gaseous sample containing toxic or harmful contaminants to a filtering means. The filtering means includes a filter tube having smaller dimensions than the filter canisters or cartridges used in protective gas masks. The filter tube contains a sample charcoal adsorbent material for adsorbing the toxic contaminants contained in the gaseous sample. Chemical analysis means are included for detecting toxic contaminants remaining in the gaseous effluent from the filtering means. Test animal chambers are also provided for exposing test animals contained therein to the gaseous effluent in order to determine the toxic effects and irritating properties of the gaseous effluent.

In accordance with the method of the present invention, a gaseous sample containing toxic or harmful contaminants is supplied to a filtering means where the gaseous sample is passed through a filter tube containing a sample charcoal adsorbent material. The gaseous effluent from the filtering means is forwarded to a chemical analyzer to chemically analyze and detect any toxic contaminants remaining in the gaseous effluent and test animals are exposed to the gaseous effluent in an enclosed area to determine the toxic effects and irritating properties of any toxic contaminants remaining in the gaseous effluent on the test animals.

Additional objects and advantages of the apparatus and method according to the present invention will become apparent from the following detailed description of the invention.

BRIEF DESCRIPTION OF THE DRAWING

The detailed description of the apparatus and method of the present invention will be more completely understood when viewed in connection with the drawings in which.

DETAILED DESCRIPTION

The present invention thus relates to an apparatus and method for evaluating the performance of a sample charcoal adsorbent material. The apparatus and method are particularly adapted for testing the effectiveness and performance of a sample charcoal adsorbent material in separating particular components from a gaseous sample. In this regard, the apparatus and method are valuable for determining the suitability of various charcoal adsorbent materials for use in protective gas masks.

Generally, the apparatus of the invention includes a supply means for supplying a gaseous sample containing harmful or toxic contaminants to a filtering means for removing the toxic contaminants from the gaseous sample. The filtering means includes a filter tube containing a sample charcoal adsorbent material which adsorbs the toxic contaminants thereon. The apparatus further includes chemical analysis means for chemically analyzing the gaseous effluent from the filtering means in order to detect any toxic contaminants remaining in the gaseous effluent. Additionally, test animal chambers are included in the apparatus for exposing test animals contained therein to the gaseous effluent from the filtering means in order to determine the toxic effects on the test animals of any toxic contaminants remaining in the gaseous effluent. The test animal chambers specifically include means for measuring respiratory changes in the test animals in order to determine any irritating effects of the gaseous effluent on the respiratory systems of the test animals.

Figure 1:
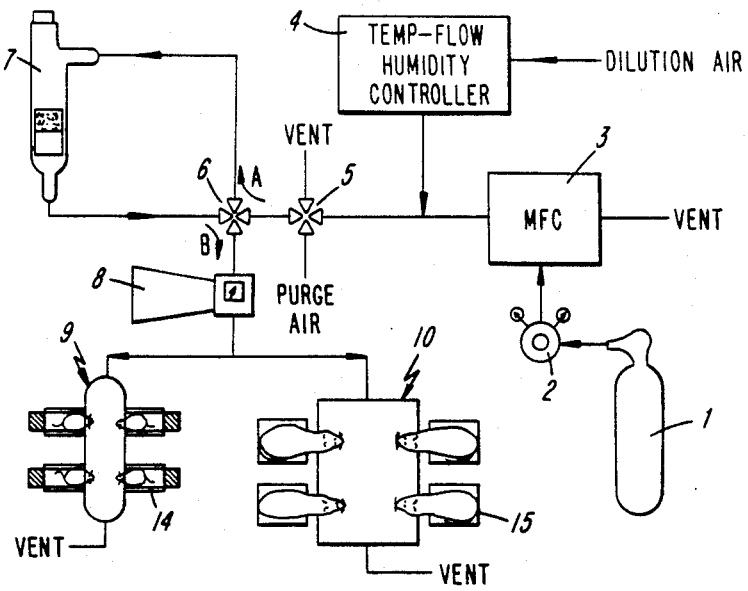
FIG. 1 is a schematic diagram of a first embodiment of the apparatus of the invention.

A first embodiment of the apparatus in accordance with the present invention is set forth in FIG. 1. The supply means for supplying a gaseous sample containing toxic contaminants as set forth in FIG. 1 comprises a gas cylinder 1 containing the test gas and a gas cylinder regulator 2. The test gas containing harmful or toxic contaminants passes through a mass flow controller 3 which controls the amount of test gas which is metered into the testing system. In a preferred embodiment, a temperature-flow-humidity controller 4 is provided in the apparatus for conditioning dilution air which may be mixed with the test gas to the desired temperature, flow and relative humidity. By controlling the temperature, flow and humidity of the dilution air, the temperature, flow and humidity of the gaseous sample which is forwarded to the filtering means may also be controlled.

Figure 3:
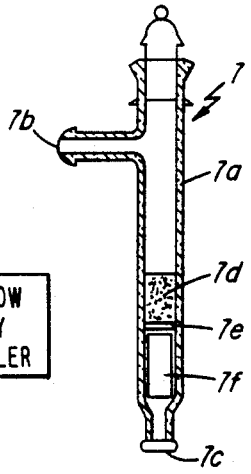
FIG. 3 is a cross sectional view of a preferred filtering means included in the apparatus of the invention.

Flow control means are provided, for example, four-way ball valves 5 and 6, for directing the gaseous sample to and from the filtering means. The filtering means 7 is disclosed in more detail in FIG. 3, and comprises a filter tube *7a* having an inlet *7b* for receiving a gaseous sample containing toxic contaminants and an outlet *7c* for delivering a filtered gaseous effluent. The filter tube *7a* may conveniently comprise a filter tube made of glass or other chemically inert material. The filter tube contains a sample of charcoal adsorbent material *7d*. The charcoal adsorbent material is retained within the filter tube by means of a porous member *7e* comprising, for example, a stainless steel screen. A glass cylinder or other block material *7f* is provided in the lower portion of the filter tube in order to provide a supporting platform for the adsorbent material. In a preferred embodiment, filter tube *7a* is of a reduced size as compared with filter canisters and cartridges used in protective gas masks and preferably has a length of about 6 to 12 inches.

Proper control of four-way ball valve 6 allows a gaseous sample to be forwarded to the filtering means 7 as shown by arrow A and gaseous effluent to be directed from the filtering means 7 to the chemical analyzer 8 as shown by arrow B. Chemical analyzer 8 analyzes the gaseous effluent from the filtering means to detect toxic contaminants remaining in the gaseous effluent. In a preferred embodiment, only a portion of the gaseous effluent from the filtering means is directed to the chemical analyzer 8 and the remaining portion of the gaseous effluent is forwarded to the test animal chambers 9 and 10. The chemical analyzer may comprise any means well known in the art for detecting components of a gaseous sample. For example, the chemical analyzer 8 may comprise an infra-red spectrometer.

The apparatus further includes test animal chambers 9 and 10 for exposing test animals contained therein to the gaseous effluent from the filtering means 7. The test animals are exposed to the gaseous effluent in order to determine any toxic or irritating effects on the test animals of any toxic contaminants remaining in the gaseous effluent. The test animal chambers also include means for measuring any respiratory changes in the test animals, which indicate irritation of the respiratory systems of the animals by the gaseous effluent. In a preferred embodiment, the means for measuring respiratory changes comprise plethysmographic boxes 14 and 15 included in the test animal chambers 9 and 10, respectively. Test animals such as mice and rats are useful in the apparatus of the invention.

Figure 2:
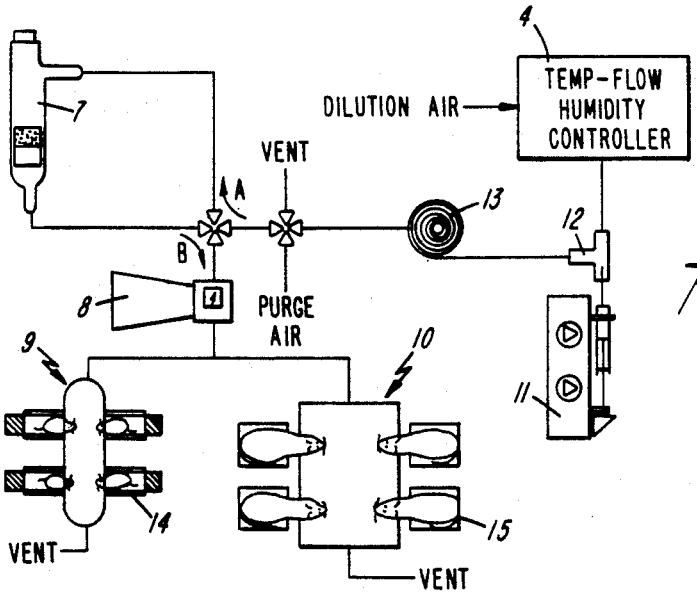
FIG. 2 is a schematic diagram of a second embodiment of the apparatus of the invention.

A second embodiment of the apparatus according to the present invention is set forth in FIG. 2 in which members corresponding to those set forth in FIG. 1 are given the same reference numerals. The embodiment of FIG. 2 differs from that of FIG. 1 in that the gaseous sample supply means includes means for vaporizing a liquid sample. Specifically, a syringe pump 11 is provided for metering a predetermined amount of a vaporizable liquid and forwarding the liquid sample to a mixing T-connector 12. T-connector 12 is included for mixing the liquid sample with a predetermined amount of dilution air from the flow-temperature-humidity controller 4. The air-liquid sample mixture is then forwarded to suitable means for vaporizing the liquid, which means 13 is disclosed in FIG. 2 as a vaporizing coil. The vaporizing means 13 ensures that the liquid sample is adequately vaporized to provide a gaseous sample before forwarding the same to the filtering means 7.

The apparatus of the invention, particularly as set forth in FIGS. 1 and 2, may conveniently be used in a method for testing the effectiveness and performance of a sample charcoal adsorbent material in accordance with the present invention. More particularly, the method of the invention comprises the steps of supplying a gaseous sample containing toxic contaminants to a filtering means including a filter tube containing a sample charcoal adsorbent material therein, passing the gaseous sample through the filtering means to remove the toxic contaminants from the gaseous sample, forwarding the gaseous effluent from the filtering means to a chemical analyzer to chemically analyze and detect any toxic contaminants remaining in the gaseous effluent and finally exposing test animals to the gaseous effluent from the filtering means in an enclosed area in order to determine the toxic effects on the test animals of any toxic contaminants remaining in the gaseous effluent.

The method of the invention may further include the preliminary step of vaporizing a liquid sample containing toxic contaminants in order to provide a gaseous sample containing toxic contaminants. Moreover, the respiratory response of the test animals to the gaseous effluent may be measured, for example by use of plethysmographic means.

Thus, the apparatus and method of the invention provide a convenient system for testing the effectiveness and performance of a sample charcoal adsorbent material in separating specific components, for example toxic contaminants, from a gaseous sample. Various charcoal adsorbent materials for use, for example, in protective gas masks may be rapidly tested using small amounts of test gas samples. Chemical analysis of the filter effluent provides detection of various toxic contaminants remaining in the gaseous effluent and the exposure of test animals to the gaseous effluent provides an indication of the toxic effects of any contaminants remaining in the gaseous effluent. A preferred method employing the apparatus of the invention is set forth below.

With reference to FIG. 1, the apparatus and method of the present invention are employed to evaluate the performance of a sample charcoal adsorbent material. A sample of a charcoal adsorbent material is inserted in the glass filter tube 7 which is then connected with the remainder of the apparatus as set forth in FIG. 1. The four-way valve 5 is adjusted to a purge position to admit purge air and the four-way valve 6 is positioned to allow the purge air to pass in the direction of arrow A into the filtering means and in the direction of arrow B out of the filtering means. Purge air is admitted to the system to purge the charcoal adsorbent material in the filter tube of any residual contaminants prior to testing. Purge air is also forwarded to the chemical analyzer 8, for example an infrared spectrometer, so that an initial instrumental baseline may be established. Test animals are placed in the respective test inhalation chambers and allowed to acclimate to the experimental surroundings so that a baseline respiration rate may also be recorded.

Once the system has been purged and the analyzer and respiration baselines have been established, the four-way valve 5 is positioned to close the purge air inlet and to receive a gaseous sample for delivering to the downstream four-way valve 6. The temperature-flow-humidity controller 4 is activated to condition air to the desired temperature and humidity and control the flow rate of the conditioned air. The test gas cylinder regulator 2 is opened and a sample test gas is metered from the cylinder 1 by adjusting the mass flow controller 3. If a vaporizable liquid sample is to be used, the syringe pump 11 in conjunction with the T-connector 12 is used to meter the test sample into the conditioned air stream. The liquid sample-air mixture is then vaporized at vaporizing means 13 to provide a gaseous sample.

The gaseous sample is then forwarded through four-way valves 5 and 6 to the filtering means 7 containing the charcoal adsorbent material. As the gaseous sample passes through the charcoal adsorbent material, toxic contaminants contained in the gaseous sample are adsorbed onto the charcoal material. At least a portion of the gaseous effluent is forwarded to the chemical analyzer 8 while the remainder of the gaseous effluent is forwarded to the test animal chambers 9 and 10 in order to expose the test animals to the gaseous effluent. This operation is continued for a sufficient period of time, for example 30 minutes, during which time the respiratory responses of the test animals are monitored, for example using plethysmographic means. The filter effluent is also monitored using the chemical analyzer.

After the challenge period, the supply of the gaseous sample is discontinued and the system is purged for an additional time period, for example 30 minutes, in order that any reversibly bound components adsorbed on the charcoal material may be desorbed. The animals are removed from the test chambers and are observed for toxic signs for an extended period, for example one week or more.

The charcoal adsorbent material contained in the filter tube 7 may be easily exchanged with other charcoal adsorbent materials in order to determine the effectiveness and performance of the various charcoal materials.

Figure 4:
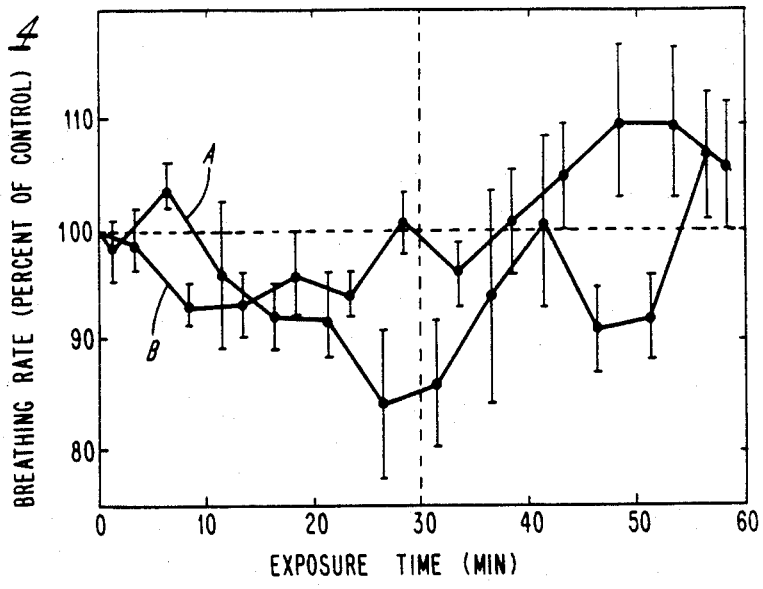
FIGS. 4 and 5 are graphical representations of measured respiratory changes in test animals in an apparatus of the invention and employing the method of the invention.
Figure 5:
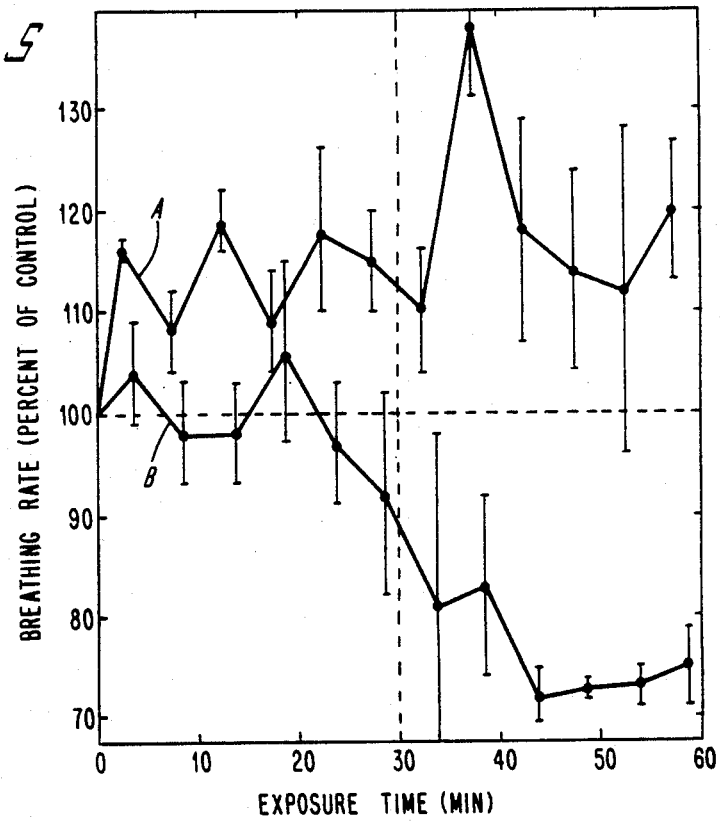

Two tests were performed in accordance with the method and apparatus of the present invention using two different types of charcoal adsorbent materials, respectively. FIGS. 4 and 5 set forth results of the respiratory response of test animals from the two tests run in accordance with the apparatus and method of the present invention. All tests represented by FIGS. 4 and 5 were conducted at a temperature of 25° C., a flow rate of 5.2 lpm and a relative humidity less than 15%. In both FIGS. 4 and 5, curves A and B represent the breathing rate of rats and mice, respectively, in relation to exposure time. FIG. 4 indicates that in the first test, using a first type of charcoal adsorbent material, there were minimal changes in the breathing rates of rats and mice when exposed to a gaseous effluent from the filtering means containing the first charcoal adsorbent material for a period of thirty minutes. Specifically, the mice evidenced little or no irritation, whereas the rats evidenced a mild irritation near the end of the thirty minute exposure period. A 100% survival rate for both rats and mice resulted, four of each rats and mice being used. Thus, the charcoal adsorbent material was effective under the conditions of this test.

In contrast, the results of FIG. 5 indicate that there were significant changes in the breathing rates of both rats and mice during the second test when exposed to the gaseous effluent from the filtering means containing a second type of charcoal adsorbent material. The data set forth in FIG. 5 suggests that an irritant, anesthetic or asphyxiant was present in the effluent from the filtering means. A 100% rat survival rate resulted, 4 of 4 survived, while a 50% mice survival rate resulted, 2 of 4 survived. Therefore, it is concluded that the second charcoal adsorbent material used in the second test was not protective under the test conditions.

Figure 6:
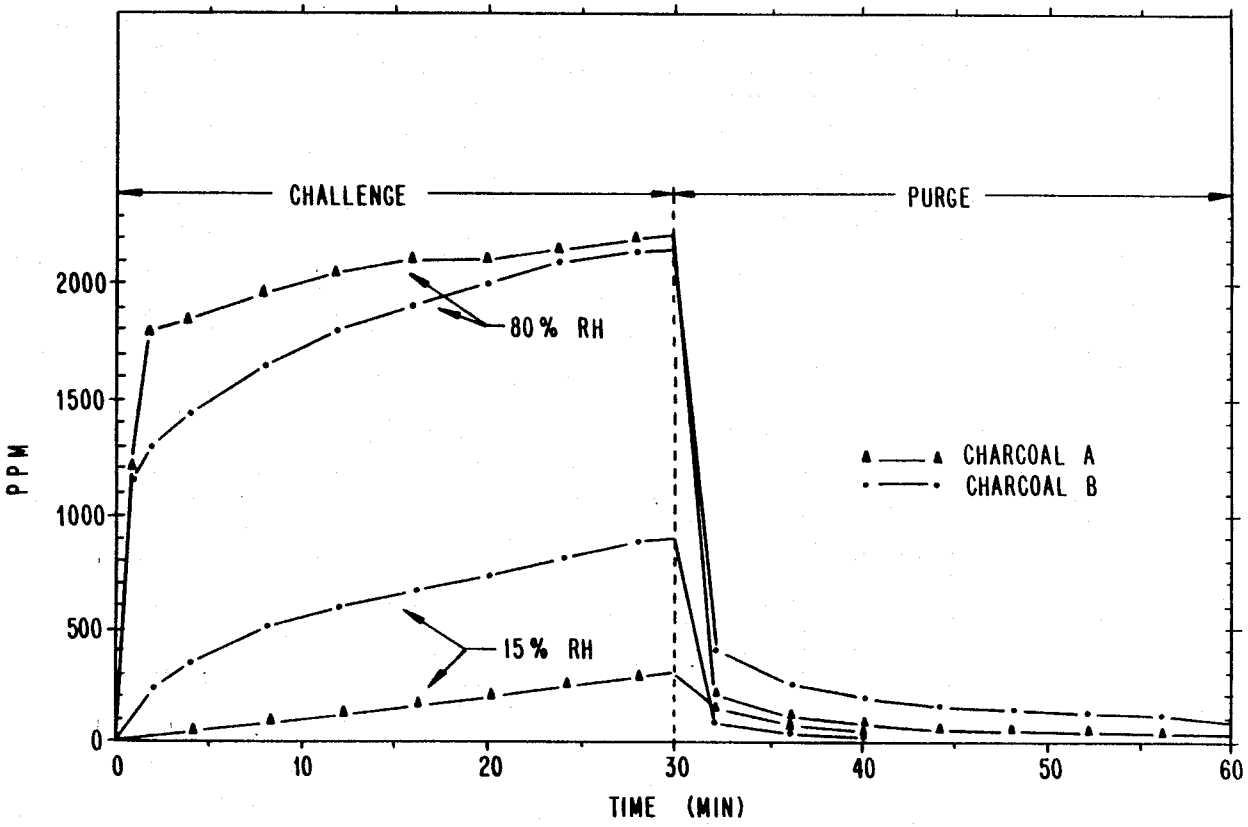
FIG. 6 is a graphical representation of the amounts of unabsorbed toxic contaminants from two different types of charcoal adsorbent materials at different humidities employed in the method and apparatus of the invention, wherein the concentration of contaminants in the filter effluent, in ppm, is plotted as a function of time, in minutes.

The temperature, flow rate and humidity of the gaseous sample which is supplied to the filtering means affects the performance of the charcoal adsorbent material contained therein. For example, additional tests were performed using two gaseous samples, respectively, which were identical except for the relative humidity of the gaseous samples. Results of these tests are set forth in FIG. 6, which discloses the concentration of contaminants not adsorbed on two types of charcoal adsorbent material in PPM versus the time of exposure of the charcoal material to the gaseous samples. Both the challenge period wherein the charcoal material is exposed to the gaseous sample and the purge period where the charcoal material is purged of any reversibly bound contaminants are set forth in FIG. 6. The measured concentration of contaminants on the different types of charcoal material, A and B, are represented in FIG. 6 by triangles and circles, respectively. Tests were performed at 15% relative humidity and 80% relative humidity and the results in FIG. 6 are so indicated. It is observed from FIG. 6 that both charcoal materials were less effective at the higher relative humidity conditions.

Thus, the apparatus and method of the present invention provide for the rapid and effective testing of the performance of various sample charcoal adsorbent materials under various test conditions.

The advantages and embodiments set forth herein are illustrative only and are not intended to limit the scope of the present invention. Additional embodiments and advantages within the scope of the present invention will be apparent to those of ordinary skill in the art.

What is claimed is:

1. An apparatus for testing the performance of a sample charcoal adsorbent material, comprising
   (a) means for supplying a gaseous sample containing contaminants to a filtering means;
   (b) filtering means for removing the toxic contaminants from the gaseous sample, said filtering means including a filter tube containing a sample charcoal adsorbent material for adsorbing thereon the toxic contaminants;
   (c) chemical analysis means for chemically analyzing the gaseous effluent from the filtering means to detect toxic contaminants remaining in the gaseous effluent; and
   (d) test animal chambers for exposing test animals contained therein to the gaseous effluent from said filtering means to determine the toxic effects on the test animals of toxic contaminants remaining in the gaseous effluent, said test animal chambers including means for measuring respiratory changes in the test animals.

2. An apparatus as defined by claim 1, wherein said gaseous sample supply means includes means for controlling the temperature, humidity and flow rate of the gaseous sample.

3. An apparatus as defined by claim 1, wherein said gaseous sample supply means includes means for vaporizing a liquid sample.

4. An apparatus as defined by claim 1, wherein said chemical analysis means comprises an infra-red spectrometer or other suitable analytical detector.

5. An apparatus as defined by claim 1, wherein said filter tube comprises a glass tube and has a length of about 6 to 12 inches.

6. An apparatus as defined by claim 1, wherein said means for measuring respiratory changes in the test animals comprises plethysmographic means.

7. A method for testing the performance of a sample charcoal adsorbent material, comprising
   (a) supplying a gaseous sample containing toxic contaminants to a filtering means;
   (b) passing the gaseous sample through a filtering means including a filter tube containing a sample charcoal adsorbent material therein to remove the toxic contaminants from the gaseous sample;
   (c) forwarding the gaseous effluent from the filtering means to a chemical analyzer to chemically analyze and detect toxic contaminants remaining in the gaseous effluent; and
   (d) exposing test animals to the gaseous effluent from the filtering means in an enclosed area to determine the toxic effects on the test animals of toxic contaminants remaining in the gaseous effluent.

8. A method as defined by claim 7, including the preliminary step of vaporizing a liquid sample containing toxic contaminants to provide a gaseous sample containing toxic contaminants.

9. A method as defined by claim 7, wherein the gaseous effluent is chemically analyzed using an infra-red spectrometer or other appropriate analytical detector.

10. A method as defined by claim 7, including the step of controlling the temperature, humidity and flow rate of the gaseous sample.

11. A method as defined by claim 7, including the further step of measuring the respiratory response of the test animals to the gaseous effluent.

12. A method as defined by claim 11, wherein the respiratory response of the test animals is measured using plethysmographic means.

13. An apparatus as defined by claim 1, wherein said chemical analysis means comprises an analytical detector.

14. A method as defined by claim 7, wherein the gaseous effluent is chemically analyzed using an analytical detector.

* * * * *